US007959910B2

(12) United States Patent
Dickey et al.

(10) Patent No.: US 7,959,910 B2
(45) Date of Patent: Jun. 14, 2011

(54) C-TERMINALLY TRUNCATED INTERFERON ALPHA VARIANTS

(75) Inventors: Lynn Dickey, Cary, NC (US); John Gasdaska, Chapel Hill, NC (US); Kevin Cox, Raleigh, NC (US)

(73) Assignee: Biolex Therapeutics, Inc., Pittsboro, NC (US)

( * ) Notice: Subject to any disclaimer, the term of this patent is extended or adjusted under 35 U.S.C. 154(b) by 814 days.

(21) Appl. No.: 10/574,046

(22) PCT Filed: Apr. 16, 2004

(86) PCT No.: PCT/US2004/011965
§ 371 (c)(1),
(2), (4) Date: Jan. 31, 2007

(87) PCT Pub. No.: WO2005/035767
PCT Pub. Date: Apr. 21, 2005

(65) Prior Publication Data
US 2007/0128162 A1  Jun. 7, 2007

(51) Int. Cl.
*A61K 38/21* (2006.01)
*C07K 14/56* (2006.01)
*C12P 21/02* (2006.01)
*C07H 21/04* (2006.01)
*C12N 5/14* (2006.01)

(52) U.S. Cl. .......... 424/85.7; 530/351; 435/69.51; 435/419; 536/23.52

(58) Field of Classification Search .......... None
See application file for complete search history.

(56) References Cited

U.S. PATENT DOCUMENTS

| | | | |
|---|---|---|---|
| 4,956,282 | A | 9/1990 | Goodman et al. |
| 5,256,410 | A | 10/1993 | Tanner et al. |
| 5,550,038 | A | 8/1996 | Goodman et al. |
| 5,629,175 | A | 5/1997 | Goodman et al. |
| 5,780,709 | A | 7/1998 | Adams et al. |
| 6,040,498 | A | 3/2000 | Stomp et al. |
| 6,096,546 | A * | 8/2000 | Raskin .......... 435/410 |
| 6,096,547 | A | 8/2000 | Goodman et al. |
| 6,288,302 | B1 | 9/2001 | Yu et al. |
| 6,610,830 | B1 | 8/2003 | Goeddel et al. |
| 6,774,283 | B1 | 8/2004 | Goodman et al. |
| 6,815,184 | B2 | 11/2004 | Stomp et al. |
| 7,161,064 | B2 | 1/2007 | Stomp et al. |
| 2003/0115640 | A1 | 6/2003 | Stomp et al. |
| 2003/0135887 | A1* | 7/2003 | Brandle et al. .......... 800/288 |
| 2003/0167531 | A1 | 9/2003 | Russell et al. |
| 2004/0073968 | A1 | 4/2004 | Stomp et al. |
| 2004/0219131 | A1 | 11/2004 | Patten et al. |
| 2005/0060776 | A1 | 3/2005 | Stomp et al. |
| 2005/0221344 | A1* | 10/2005 | Welcher et al. .......... 435/6 |
| 2006/0024272 | A1 | 2/2006 | Reinl et al. |
| 2006/0195946 | A1 | 8/2006 | Dickey et al. |
| 2007/0044177 | A1 | 2/2007 | Stomp et al. |
| 2009/0025106 | A1 | 1/2009 | Reinl et al. |
| 2009/0282584 | A1 | 11/2009 | Stomp et al. |

FOREIGN PATENT DOCUMENTS

| | | |
|---|---|---|
| AT | 393690 B | 11/1991 |
| EP | 0032134 B2 | 7/1981 |
| EP | 0141484 A2 | 5/1985 |
| EP | 0 194 006 A1 | 9/1986 |
| EP | 0 256 424 A1 | 2/1988 |
| WO | WO 99/07210 | 2/1999 |
| WO | WO 01/36001 A2 | 5/2001 |
| WO | WO 02/10414 A2 | 2/2002 |
| WO | WO 02/43650 A2 | 6/2002 |
| WO | WO 03/002152 A2 | 1/2003 |
| WO | WO 2004/046365 A2 | 6/2004 |

OTHER PUBLICATIONS

Ackerman, S.K., et al., Biologic Activity in a Fragment of Recombinant Human Interferon α, *Proc. Natl. Acad. Sci., USA*, 1984, pp. 1045-1047, vol. 81.
Arnheiter, H., et al., "Orientation of a Human Leukocyte Interferon Molecule on its Cell Surface Receptor: Carboxyl Terminus Remains Accessible to a Monoclonal Antibody Made Against a Synthetic Interferon Fragment," *Proc. Natl. Acad. Sci., USA*, 1983, pp. 2539-2543, vol. 80.
Chang, N.T., et al., "Synthesis of a Human Leukocyte Interferon with a Modified Carboxy Terminus in *Escherichia coli*," *Archives of Biochemistry and Biophysics*, 1983, pp. 585-589, vol. 221(2).
Cheetham, B.F., et al., "Structure-Function Studies of Human Interferons-α Enhanced Activity on Human and Murine Cells," *Antiviral Research*, 1991, pp. 27-40, vol. 15.
Franke, A.E., et al., "Carboxyterminal Region of Hybrid Leukocyte Interferons Affects Antiviral Specificity," *DNA*, 1982, vol. 1(3).
Gasdaska, J.R., et al., Advantages of Therapeutic Protein Production in the Aquatic Plant Lemna, www.bioprocessingjournal.com, Mar./Apr. 2003.
Levy, W.P., et al., "Amino Acid Sequence of a Human Leukocyte Interferon," *Proc. Natl. Acad. Sci, USA*, 1981, pp. 6186-6190, vol. 78(10).
Chang, et al., "Evolution of a cytokine using DNA family shuffling", *Nature Biotech*. (1999) 17:793-797.
Döbeli, H. et al., "Role of the carboxyl-terminal sequence on the biological activity of human immune interferon (IFN-Gamma)," *Journal of Biotechnology*, 1988, vol. 7(3), pp. 199-216.
Horisberger, M. et al., "Interferon-Alpha Hybrids," *Pharmacology & Therapeutics*, 1995, vol. 66(3), pp. 507-534.
Houghton, "Human Interferon Gene Sequences," *Nature*, 1980, vol. 285(5766), pp. 536.

(Continued)

*Primary Examiner* — Robert Landsman
*Assistant Examiner* — Bruce D Hissong
(74) *Attorney, Agent, or Firm* — Alston & Bird LLP

(57) ABSTRACT

The present invention provides biologically active variants of human α-2b-interferon. The variants contain carboxy terminus truncations when compared with the amino acid sequence of full-length human α-2b-interferon. It is the novel finding of the present invention that these truncated variants have the biological activity of full-length human α-2b-interferon. The invention encompasses these biologically active variant α-interferons, as well as polynucleotides encoding these interferons. Expression cassettes comprising these polynucleotides and host cells comprising the expression cassettes are also provided. The invention also provides compositions comprising variant α-interferon polypeptides and a pharmaceutically acceptable carrier.

10 Claims, 2 Drawing Sheets

OTHER PUBLICATIONS

Mantei, et al., "The nucleotide sequence of a cloned human leukocyte interferon cDNA", *Gene* (1980) 10:1-10.

Mantei, et al., "The nucleotide sequence of a cloned human leukocyte interferon cDNA", *Chemical Abstracts* (1980) 93:489, Abstract No. 130319s.

Nacheva, G. et al., "Human interferon gamma: significance of the C-terminal flexible domain for its biological activity," *Archives of Biochemistry and Biophysics*, 2003, vol. 413(1), pp. 91-981.

Nagata, et al., "The structure of one of the eight or more distinct chromosomal genes for human intereferon-alpha", *Nature* (1980) 287(5781):401-408.

Nagata, et al., "Synthesis in *E. coli* of a polypeptide with human leukocyte interferon activity", *Chemical Abstracts* (1980) 93:479, Abstract No. 41286m.

Nagata, et al., "Synthesis in *E. coli* of a polypeptide with human leukocyte interferon activity", *Nature* (1980) 284:316-320.

Ozes, et al., "A comparison of Interferon-Con1 with natural recombinant interferons-alpha: antiviral, antiproliferative, and natural killer-inducing activities", *J. Interferon Res.* (1992) 12:55-59.

Pestka and Langer, "Interferons and their actions", *Ann. Rev. Biochem.* (1987) 56:727-77.

Platis and Foster, "High yield expression, refolding, and characterization of recombinant interferon α2/α8 hybrids in *Escherichia coli*", *Protein Expression and Purfication* (2003) 31:222-230.

Rubinstein, et al., "Human leukocyte interferon: isolation and characterization of several molecular forms", *Arch. of Biochem. and Biophysics* (1981) 210:307-318.

Rubinstein, et al., "Human leukocyte interferon purified to homogeneity", *Science* (1978) 202(4374):1289-1290.

Rubinstein, et al., "Human leukocyte interferon: production, purification to homogeneity, and initial characterization", *Proc. Natl. Acad. Sci. USA* (1979) 76(2):640-644.

Schilliberg, et al., "Review—Molecular Farming of Recombinant Antibodies in Plants," (2003) *CMLA, Cell. Mol. Life Sci.* 60:433-445.

Streuli, et al., "At least three human type alpha interferons: structure of alpha 2", *Science* (1980) 209(4463):1343-1347.

Sugyiama, et al., "Expression of Human Interferon-a2 in Sf9 Cells," *Dur. J. Biochem.* (1993) 271:921-927.

Taniguchi, et al., "Expression of the Human Fibroblast Interferon Gene in *Escherichia coli*", *Proc. Natl. Acad. Sci. USA* (1980) 77(9):5230-5233.

Taniguchi, et al., "Human leukocyte and fibroblast interferons are structurally related", *Nature* (1980) 285:547-549.

Torma and Paucker, "Purification and characterization of human leukocyte interferon components", *J. Biol. Chem.* (1976) 251(16):4810-4816.

Weissmann, "The cloning of interferon and other mistakes", *Interferon* (1981) 3:101-134.

Zoon, et al., "Amino terminal sequence of the major component of human lymphoblastoid interferon", *Science* (1980) 207(4430):527-528.

Zoon, et al., "Purification and partial characterization of human lymphoblastoid interferon", *Proc. Natl. Acad. Sci. USA* (1979) 76(11):5601-5605.

Zoon, et al., "Human lymphoblastoid interferon: purification, amino acid composition, and amino-terminal sequence", *Ann. NY Acad. Sci.* (1980) 350:390-398.

Zhu, et al., "Expression of Human a-Interferon cDNA in Transgenic Rice Plants," *Plant Cell, Tissue and Organ Culture* (1994) 36:197-204.

\* cited by examiner

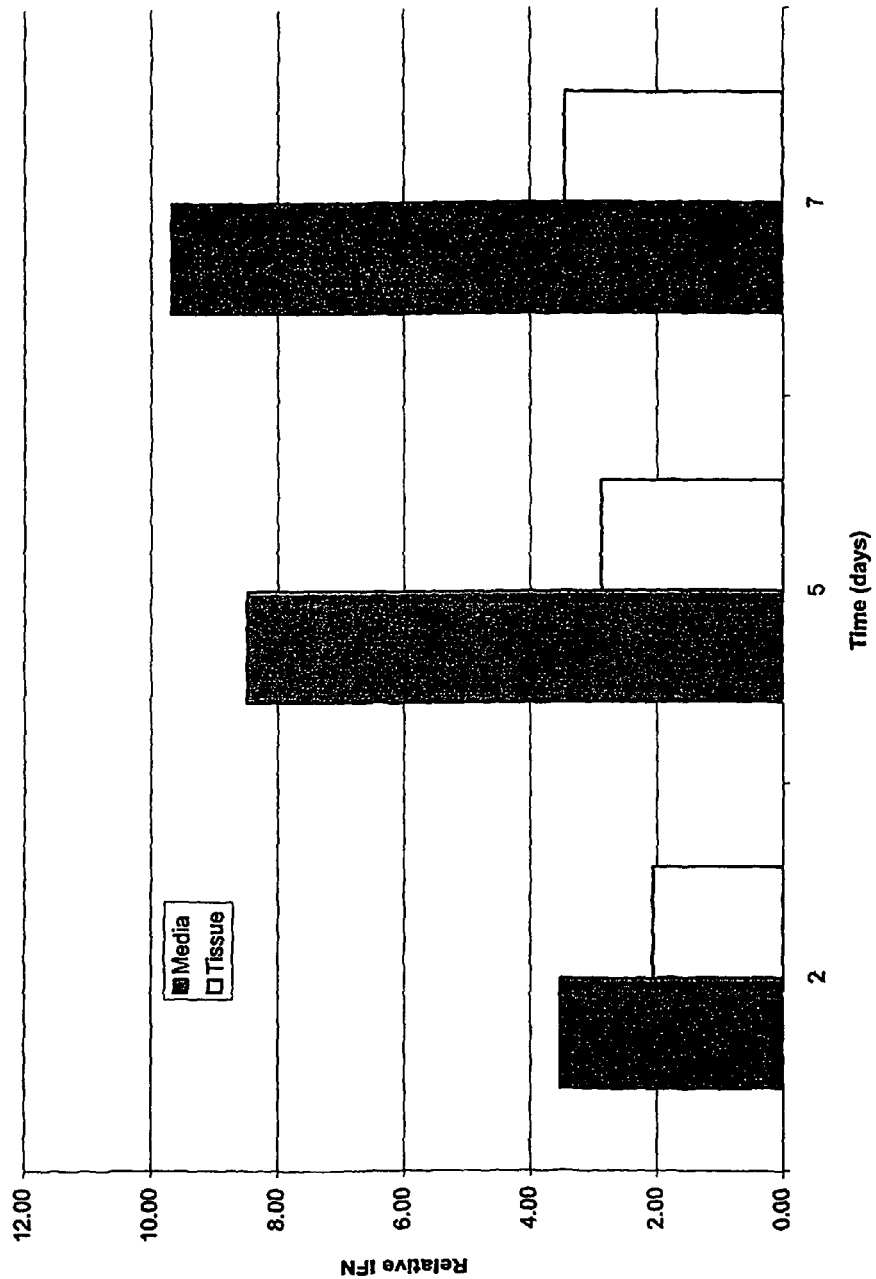

SEQUENCE LISTING

```
<160> NUMBER OF SEQ ID NOS: 12

<210> SEQ ID NO 1
<211> LENGTH: 184
<212> TYPE: PRT
<213> ORGANISM: Artificial Sequence
<220> FEATURE:
<223> OTHER INFORMATION: Truncated variant of human alpha-2b-interferon
      precursor

<400> SEQUENCE: 1

Met Ala Leu Thr Phe Ala Leu Leu Val Ala Leu Leu Val Leu Ser Cys
 1               5                  10                  15

Lys Ser Ser Cys Ser Val Gly Cys Asp Leu Pro Gln Thr His Ser Leu
                20                  25                  30

Gly Ser Arg Arg Thr Leu Met Leu Leu Ala Gln Met Arg Arg Ile Ser
            35                  40                  45

Leu Phe Ser Cys Leu Lys Asp Arg His Asp Phe Gly Phe Pro Gln Glu
        50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
                100                 105                 110

Gln Gln Leu Asn Asp Leu Glu Ala Cys Val Ile Gln Gly Val Gly Val
            115                 120                 125

Thr Glu Thr Pro Leu Met Lys Glu Asp Ser Ile Leu Ala Val Arg Lys
        130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser Leu
            180

<210> SEQ ID NO 2
<211> LENGTH: 183
<212> TYPE: PRT
<213> ORGANISM: Artificial Sequence
<220> FEATURE:
<223> OTHER INFORMATION: Truncated variant of human alpha-2b-interferon
      precursor

<400> SEQUENCE: 2

Met Ala Leu Thr Phe Ala Leu Leu Val Ala Leu Leu Val Leu Ser Cys
 1               5                  10                  15

Lys Ser Ser Cys Ser Val Gly Cys Asp Leu Pro Gln Thr His Ser Leu
```

```
                 20                  25                  30
Gly Ser Arg Arg Thr Leu Met Leu Leu Ala Gln Met Arg Arg Ile Ser
             35                  40                  45

Leu Phe Ser Cys Leu Lys Asp Arg His Asp Phe Gly Phe Pro Gln Glu
 50                  55                  60

Glu Phe Gly Asn Gln Phe Gln Lys Ala Glu Thr Ile Pro Val Leu His
 65                  70                  75                  80

Glu Met Ile Gln Gln Ile Phe Asn Leu Phe Ser Thr Lys Asp Ser Ser
                 85                  90                  95

Ala Ala Trp Asp Glu Thr Leu Leu Asp Lys Phe Tyr Thr Glu Leu Tyr
                100                 105                 110

Gln Gln Leu Asn Asp Leu Glu Ala Cys Val Ile Gln Gly Val Gly Val
                115                 120                 125

Thr Glu Thr Pro Leu Met Lys Glu Asp Ser Ile Leu Ala Val Arg Lys
                130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu Ser
                180

<210> SEQ ID NO 3
<211> LENGTH: 182
<212> TYPE: PRT
<213> ORGANISM: Artificial Sequence
<220> FEATURE:
<223> OTHER INFORMATION: Truncated variant of human alpha-2b-interferon
      precursor

<400> SEQUENCE: 3

Met Ala Leu Thr Phe Ala Leu Leu Val Ala Leu Leu Val Leu Ser Cys
 1               5                  10                  15

Lys Ser Ser Cys Ser Val Gly Cys Asp Leu Pro Gln Thr His Ser Leu
                 20                  25                  30

Gly Ser Arg Arg Thr Leu Met Leu Leu Ala Gln Met Arg Arg Ile Ser
             35                  40                  45

Leu Phe Ser Cys Leu Lys Asp Arg His Asp Phe Gly Phe Pro Gln Glu
 50                  55                  60

Glu Phe Gly Asn Gln Phe Gln Lys Ala Glu Thr Ile Pro Val Leu His
 65                  70                  75                  80

Glu Met Ile Gln Gln Ile Phe Asn Leu Phe Ser Thr Lys Asp Ser Ser
                 85                  90                  95

Ala Ala Trp Asp Glu Thr Leu Leu Asp Lys Phe Tyr Thr Glu Leu Tyr
                100                 105                 110

Gln Gln Leu Asn Asp Leu Glu Ala Cys Val Ile Gln Gly Val Gly Val
                115                 120                 125

Thr Glu Thr Pro Leu Met Lys Glu Asp Ser Ile Leu Ala Val Arg Lys
                130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln Glu
                180
```

```
<210> SEQ ID NO 4
<211> LENGTH: 181
<212> TYPE: PRT
<213> ORGANISM: Artificial Sequence
<220> FEATURE:
<223> OTHER INFORMATION: Truncated variant of human alpha-2b-interferon
      precursor

<400> SEQUENCE: 4
```

Met Ala Leu Thr Phe Ala Leu Leu Val Ala Leu Leu Val Leu Ser Cys
 1               5                  10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu Gln
            180

```
<210> SEQ ID NO 5
<211> LENGTH: 180
<212> TYPE: PRT
<213> ORGANISM: Artificial Sequence
<220> FEATURE:
<223> OTHER INFORMATION: Trucated varaint of human alpha-2b-interferon
      precursor

<400> SEQUENCE: 5
```

Met Ala Leu Thr Phe Ala Leu Leu Val Ala Leu Leu Val Leu Ser Cys
 1               5                  10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

```
Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160

Cys Ala Trp Glu Val Val Arg Ala Glu Ile Met Arg Ser Phe Ser Leu
                165                 170                 175

Ser Thr Asn Leu
            180

<210> SEQ ID NO 6
<211> LENGTH: 161
<212> TYPE: PRT
<213> ORGANISM: Artificial Sequence
<220> FEATURE:
<223> OTHER INFORMATION: Truncated variant of mature human
      alpha-2b-interferon

<400> SEQUENCE: 6

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
            115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu

<210> SEQ ID NO 7
<211> LENGTH: 160
<212> TYPE: PRT
<213> ORGANISM: Artificial Sequence
<220> FEATURE:
<223> OTHER INFORMATION: Truncated variant of mature human
      alpha-2b-interferon

<400> SEQUENCE: 7

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
```

```
65                  70                  75                  80
Leu Asp Lys Phe Tyr Thr Glu Leu Tyr Gln Gln Leu Asn Asp Leu Glu
                    85                  90                  95

Ala Cys Val Ile Gln Gly Val Gly Val Thr Glu Thr Pro Leu Met Lys
                100                 105                 110

Glu Asp Ser Ile Leu Ala Val Arg Lys Tyr Phe Gln Arg Ile Thr Leu
                115                 120                 125

Tyr Leu Lys Glu Lys Lys Tyr Ser Pro Cys Ala Trp Glu Val Val Arg
            130                 135                 140

Ala Glu Ile Met Arg Ser Phe Ser Leu Ser Thr Asn Leu Gln Glu Ser
145                 150                 155                 160

<210> SEQ ID NO 8
<211> LENGTH: 159
<212> TYPE: PRT
<213> ORGANISM: Artificial Sequence
<220> FEATURE:
<223> OTHER INFORMATION: Truncated variant of mature human
      alpha-2b-interferon

<400> SEQUENCE: 8

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
        50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                    85                  90                  95

Ala Cys Val Ile Gln Gly Val Gly Val Thr Glu Thr Pro Leu Met Lys
                100                 105                 110

Glu Asp Ser Ile Leu Ala Val Arg Lys Tyr Phe Gln Arg Ile Thr Leu
                115                 120                 125

Tyr Leu Lys Glu Lys Lys Tyr Ser Pro Cys Ala Trp Glu Val Val Arg
            130                 135                 140

Ala Glu Ile Met Arg Ser Phe Ser Leu Ser Thr Asn Leu Gln Glu
145                 150                 155

<210> SEQ ID NO 9
<211> LENGTH: 158
<212> TYPE: PRT
<213> ORGANISM: Artificial Sequence
<220> FEATURE:
<223> OTHER INFORMATION: Truncated variant of mature human
      alpha-2b-interferon.

<400> SEQUENCE: 9

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
        50                  55                  60
```

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln
145                 150                 155

<210> SEQ ID NO 10
<211> LENGTH: 157
<212> TYPE: PRT
<213> ORGANISM: Artificial Sequence
<220> FEATURE:
<223> OTHER INFORMATION: Truncated variant of mature human
      alpha-2b-interferon.

<400> SEQUENCE: 10

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu
145                 150                 155

<210> SEQ ID NO 11
<211> LENGTH: 498
<212> TYPE: DNA
<213> ORGANISM: Artificial Sequence
<220> FEATURE:
<223> OTHER INFORMATION: Duckweed codon optimized sequence encoding
      mature human alpha-2b interferon
<220> FEATURE:
<221> NAME/KEY: CDS
<222> LOCATION: (1)...(498)

<400> SEQUENCE: 11 tgc gac ctc ccc cag acc cac agc ctc ggg tcc cgc cgc acc ctc atg    48
Cys Asp Leu Pro Gln Thr His Ser Leu Gly Ser Arg Arg Thr Leu Met
1               5                   10                  15 ctg ctg gcg cag atg cgc cgc atc tcg ctc ttc agc tgc ctg aag gac    96
Leu Leu Ala Gln Met Arg Arg Ile Ser Leu Phe Ser Cys Leu Lys Asp

```
                    20              25              30
cgc cac gac ttc ggc ttc ccg cag gag gag ttc ggc aac cag ttc cag    144
Arg His Asp Phe Gly Phe Pro Gln Glu Glu Phe Gly Asn Gln Phe Gln
         35              40              45 aag gcc gag acg atc ccc gtg ctc cac gag atg atc cag cag atc ttc    192
Lys Ala Glu Thr Ile Pro Val Leu His Glu Met Ile Gln Gln Ile Phe
     50              55              60 aac ctg ttc agc acc aag gac agc tcg gcc gcc tgg gac gag acc ctg    240
Asn Leu Phe Ser Thr Lys Asp Ser Ser Ala Ala Trp Asp Glu Thr Leu
 65              70              75              80 ctc gac aag ttc tac acc gag ctg tac cag cag ctc aac gac ctg gag    288
Leu Asp Lys Phe Tyr Thr Glu Leu Tyr Gln Gln Leu Asn Asp Leu Glu
             85              90              95 gcg tgc gtg atc cag ggg gtt ggg gtt acg gag acg ccg ctg atg aag    336
Ala Cys Val Ile Gln Gly Val Gly Val Thr Glu Thr Pro Leu Met Lys
        100             105             110 gag gac agc atc ctc gcc gtg cgc aag tac ttc cag cgc atc acg ctc    384
Glu Asp Ser Ile Leu Ala Val Arg Lys Tyr Phe Gln Arg Ile Thr Leu
    115             120             125 tac ctc aag gag aag aag tac agc ccg tgc gcc tgg gag gtc gtt cgc    432
Tyr Leu Lys Glu Lys Lys Tyr Ser Pro Cys Ala Trp Glu Val Val Arg
    130             135             140 gcc gag atc atg cgc tcc ttc agc ctg agc acc aac ctc cag gag agc    480
Ala Glu Ile Met Arg Ser Phe Ser Leu Ser Thr Asn Leu Gln Glu Ser
145             150             155             160 ctc cgc tcc aag gag taa                                            498
Leu Arg Ser Lys Glu *
                165

<210> SEQ ID NO 12
<211> LENGTH: 23
<212> TYPE: PRT
<213> ORGANISM: Homo sapiens

<400> SEQUENCE: 12

Met Ala Leu Thr Phe Ala Leu Leu Val Ala Leu Leu Val Leu Ser Cys
 1               5                  10                  15

Lys Ser Ser Cys Ser Val Gly
             20
```

C-TERMINALLY TRUNCATED INTERFERON ALPHA VARIANTS

FIELD OF THE INVENTION

The present invention relates to biologically active variants of human alpha interferon.

BACKGROUND OF THE INVENTION

The interferons are a family of glycoproteins whose secretion from cells is induced by a number of signals including viruses, double-stranded RNAs, other polynucleotides, antigens, and mitogens. Interferons exhibit multiple biological activities, including antiviral, antiproliferative, and immunomodulatory activities. At least three distinct types of human interferons, α, β, and γ, have been distinguished based on a number of factors, including anti-viral and anti-proliferative activities.

α-interferons act through interaction with cell-surface receptors and induce the expression, primarily at the transcriptional level, of a broad but specific set of cellular genes. Several INTERFERON-induced gene products have been used as markers for the biological activity of interferons. These include, for instance, ISG15, ISG54, IRF1, GBP, and IP10.

Assays for interferon-mediated anti-viral activity have been described in the art. See, for example, McNeill, (1981) *J Immunol Methods.* 46:121-7. Assays for interferon antiviral activity include inhibition of cytopathic effect, virus plaque formation; and reduction of virus yield. Viral cytopathic effect assays measure the degree of protection induced in cell cultures pretreated with interferon INTERFERON and subsequently infected with viruses. See, for example, Rubinstein et al. (1981) *J Virol.* 37:755-8. Plaque-reduction assays can be used to measure the resistance of INTERFERON-treated cell cultures to a plaque-forming virus (for instance, measles virus). Finally, virus yield assays measure the amount of virus released from cells during, for instance, a single growth cycle. Such assays are useful for testing the antiviral activity of INTERFERONs against viruses that do not cause cytopathic effects, or that do not build plaques in target-cell cultures.

α-2b interferons have since been shown to be efficacious against viral, proliferative, and inflammatory disorders, including malignant melanoma, hairy cell leukemia, chronic hepatitis B, chronic hepatitis C, condylomata acuminata, follicular (non-Hodgkin's) lymphoma, and AIDS-related Kaposi's sarcoma. Clinical uses of interferons are reviewed in Gresser (1997) *J. Leukoc. Biol.* 61:567-74, and Pfeffer (1997) *Semin Oncol.* 24(3 Suppl 9):S9-63-S9-69.

SUMMARY OF THE INVENTION

The present invention provides biologically active variants of human α-2b-interferon. The variants contain carboxy terminus truncations when compared with the amino acid sequence of full-length human α-2b-interferon. It is the novel finding of the present invention that these truncated variants have the biological activity of human α-2b-interferon. The sequences of the α-2b-interferon variant precursor polypeptides are shown in SEQ ID NOS:1-5, while the sequences of the mature α-2b-interferon variant polypeptides s are shown in SEQ ID NOS:6-10. Accordingly, in one embodiment, the invention provides a purified polypeptide consisting of an amino acid sequence selected from the amino acid sequences shown in SEQ ID NOS:1-10.

In some embodiments, the polypeptide consisting of a signal peptide operably linked to an amino acid sequence selected from the sequences shown in SEQ ID NOS:6-10. In some embodiments, the signal peptide is a mammalian signal peptide, while in other embodiments, the signal peptide is a plant signal peptide.

In one aspect of the invention, the polypeptides of the invention are recombinantly produced in a host cell plant cell. In particular embodiments, the host cell is a mammalian cell, a plant cell, a yeast cell, an insect cell, or a prokaryotic cell.

The invention also encompasses polynucleotides encoding the polypeptide of the invention, expression cassettes comprising these polynucleotides, and host cells comprising the expression cassettes.

In another embodiment, the invention provides a composition comprising a purified polypeptide of the invention and a pharmaceutically acceptable carrier.

BRIEF DESCRIPTION OF THE DRAWINGS

FIG. 2 show the interferon levels (as determined by a solid phase sandwich immunoassay) in the media and tissue of a transformed duckweed cultures, as described in Example 2.

DETAILED DESCRIPTION OF THE INVENTION

Figure 1:
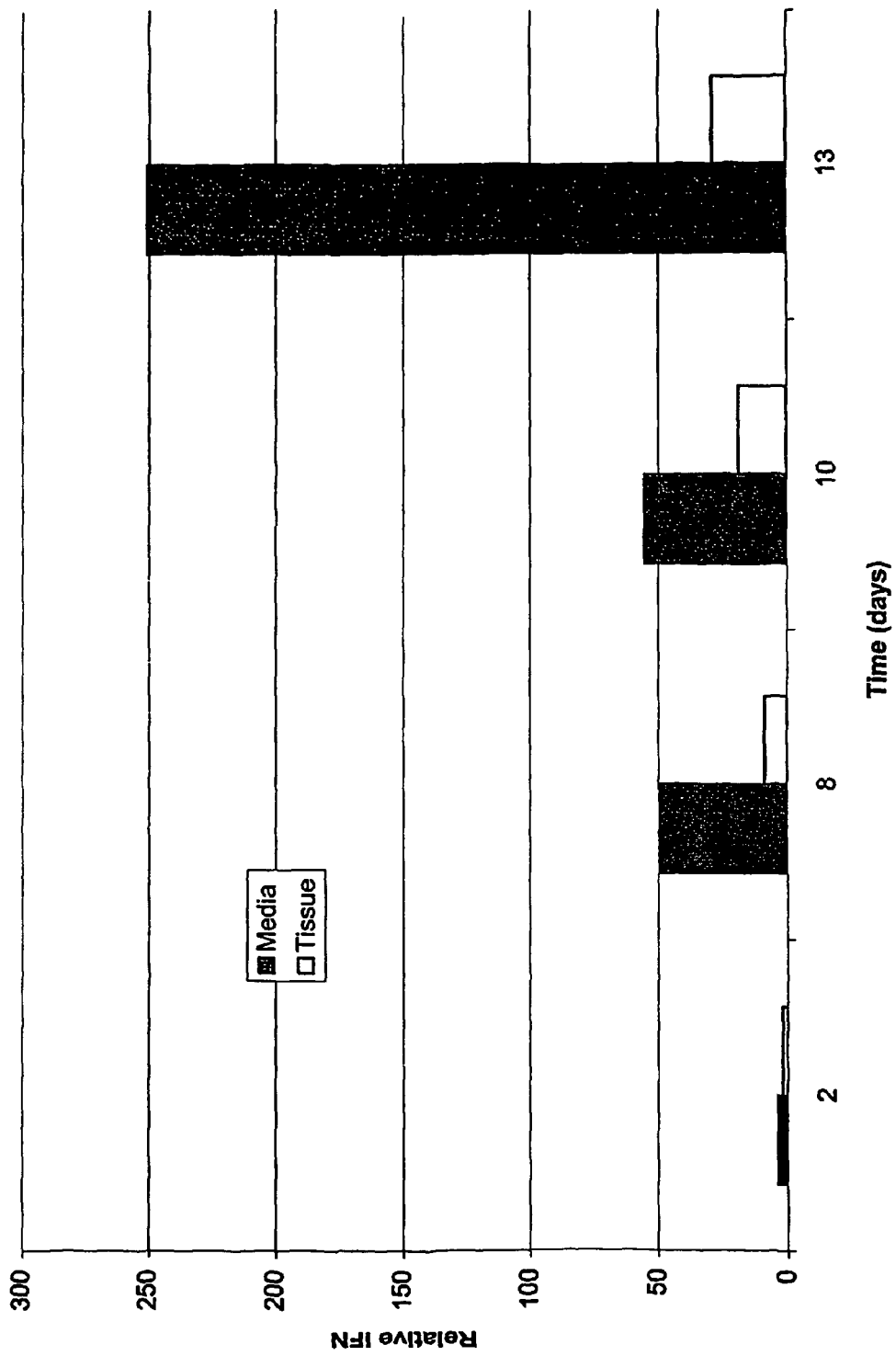
FIG. 1 show the interferon levels (as determined by a solid phase sandwich immunoassay) in the media and tissue of a transformed duckweed culture, as described Example 1.

The present invention provides biologically active variants of human α-2b-interferon. The variants contain carboxy terminus truncations when compared with the amino acid sequence of full-length human α-2b-interferon. It is the novel finding of the present invention that these truncated variants have the biological activity of human α-2b-interferon. The present invention provides the sequences of these α-2b interferon variants.

DEFINITIONS

An "isolated" or "purified" polynucleotide or polypeptide is substantially or essentially free from components that normally accompany or interact with the polynucleotide or protein as found in its naturally occurring environment. Thus, an isolated or purified polynucleotide or polypeptide is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-polypeptide-of-interest chemicals.

A "biologically active polypeptide" refers to a polypeptide that has the capability of performing one or more biological functions or a set of activities normally attributed to the polypeptide in a biological context. Those skilled in the art will appreciate that the term "biologically active" includes polypeptides in which the biological activity is altered as compared with the native protein (e.g., suppressed or enhanced), as long as the protein has sufficient activity to be of interest for use in industrial or chemical processes or as a therapeutic, vaccine, or diagnostics reagent. Biological activity can be determined by any method available in the art. For example, the biological activity of members of the interferon family of proteins can be determined by any of a number of methods including their interaction with interferon-specific antibodies, their ability to increase resistance to viral infection, or their ability to modulate the transcription of interferon-regulated gene targets. Examples of such methods are described elsewhere herein.

The terms "expression" or "production" refer to the biosynthesis of a gene product, including the transcription, translation, and assembly of said gene product.

By "recombinantly produced" is intended a polypeptide that has been prepared by recombinant DNA techniques. Recombinantly produced interferon variants can be produced by culturing a host cell transformed with an expression cassette comprising a polynucleotide that encodes an α-interferon variant of the invention. The host cell is one that can transcribe the nucleotide sequence and produce the desired protein, and can be prokaryotic (for example, *E. coli*) or eukaryotic (for example a plant, yeast, insect, or mammalian cell).

The term "duckweed" refers to members of the family Lemnaceae. This family currently is divided into five genera and 38 species of duckweed as follows: genus *Lemna* (*L. aequinoctialis, L. disperma, L. ecuadoriensis, L. gibba, L. japonica, L. minor, L. miniscula, L. obscura, L. perpusilla, L. tenera, L. trisulca, L. turionifera, L. valdiviana*); genus *Spirodela* (*S. intermedia, S. polyrrhiza*); genus *Wolfia* (*Wa. angusta, Wa. arrhiza, Wa. australina, Wa. borealis, Wa. brasiliensis, Wa. columbiana, Wa. elongata, Wa. globosa, Wa. microscopica, Wa. neglecta*) genus *Wolfiella* (*Wl. caudata, Wl. denticulata, Wl. gladiata, Wl. hyalina, Wl. lingulata, Wl. repunda, Wl. rotunda, and Wl. neotropica*), and genus *Landoltia* (*L. punctata*). Any other genera or species of Lemnaceae, if they exist, are also aspects of the present invention. *Lemna* species can be classified using the taxonomic scheme described by Les et al. (2002) *Systematic Botany* 27:221-40.

"Operably linked" as used herein in reference to nucleotide sequences refers to multiple nucleotide sequences that are placed in a functional relationship with each other. Generally, operably linked DNA sequences are contiguous and, where necessary to join two protein coding regions, in reading frame.

A. Polypeptides.

The present invention identifies biologically active variants of human α-2b interferon. These variants contain carboxy terminus truncations of 4-8 amino acids in comparison with full-length human α-2b-interferon. The sequences of the mature forms of these biologically active interferon variants are provided in SEQ ID NOS:6-10, while the corresponding sequences of the interferon variant precursor polypeptides are provided in SEQ ID NOS:1-5.

In some embodiments, the invention encompasses compositions comprising a mixture of two or more α-interferon variants of the invention. Such mixtures may comprise two or more, three or more, four or more, five or more, or more than six of the α-interferon variants consisting of the amino acid sequences set forth in SEQ ID NOS:1-10.

B. Polynucleotides and Expression Cassettes

In one aspect the present invention provides polynucleotides encoding the biologically active α-interferons of the invention. Accordingly, the invention encompasses polynucleotides encoding polypeptides consisting of the amino acid sequences set forth in SEQ ID NOS:1-10.

In some embodiments, the polynucleotides may be comprised within an expression cassette. The expression cassette comprises a transcriptional initiation region linked to the nucleic acid or gene of interest. Such an expression cassette can be provided with a plurality of restriction sites for insertion of the polynucleotide of interest to be under the transcriptional regulation of the regulatory regions.

The transcriptional initiation region, (e.g., a promoter) may be native or homologous or foreign or heterologous to the host, or could be the natural sequence or a synthetic sequence. By foreign, it is intended that the transcriptional initiation region is not found in the wild-type host into which the transcriptional initiation region is introduced. As used herein a chimeric gene comprises a coding sequence operably linked to a transcription initiation region that is heterologous to the coding sequence.

Any suitable promoter known in the art can be employed according to the present invention (including bacterial, yeast, fungal, insect, mammalian, and plant promoters). For example, plant promoters may be used. Exemplary promoters include, but are not limited to, the Cauliflower Mosaic Virus 35S promoter, the opine synthetase promoters (e.g., nos, mas, ocs, etc.), the ubiquitin promoter, the actin promoter, the ribulose bisphosphate (RubP) carboxylase small subunit promoter, and the alcohol dehydrogenase promoter. The duckweed RubP carboxylase small subunit promoter is known in the art (Silverthorne et al. (1990) *Plant Mol. Biol.* 15:49). Other promoters from viruses that infect plants, preferably duckweed, are also suitable including, but not limited to, promoters isolated from Dasheen mosaic virus, Chlorella virus (e.g., the Chlorella virus adenine methyltransferase promoter; Mitra et al. (1994) *Plant Mol. Biol.* 26:85), tomato spotted wilt virus, tobacco rattle virus, tobacco necrosis virus, tobacco ring spot virus, tomato ring spot virus, cucumber mosaic virus, peanut stump virus, alfalfa mosaic virus, sugarcane baciliform badnavirus and the like.

The overall strength of a given promoter can be influenced by the combination and spatial organization of cis-acting nucleotide sequences such as upstream activating sequences. For example, activating nucleotide sequences derived from the *Agrobacterium tumefaciens* octopine synthase gene can enhance transcription from the *Agrobacterium tumefaciens* mannopine synthase promoter (see U.S. Pat. No. 5,955,646 to Gelvin et al.). In the present invention, the expression cassette can contain activating nucleotide sequences inserted upstream of the promoter sequence to enhance the expression of the nucleotide sequence of interest. In one embodiment, the expression cassette includes three upstream activating sequences derived from the *Agrobacterium tumefaciens* octopine synthase gene operably linked to a promoter derived from an *Agrobacterium tumefaciens* mannopine synthase gene (see U.S. Pat. No. 5,955,646, herein incorporated by reference).

The expression cassette may include in the 5'-3' direction of transcription, a transcriptional and translational initiation region, a polynucleotide of interest, and a transcriptional and translational termination region functional in plants. Any suitable termination sequence known in the art may be used in accordance with the present invention. The termination region may be native with the transcriptional initiation region, may be native with the nucleotide sequence of interest, or may be derived from another source. Convenient termination regions are available from the Ti-plasmid of *A. tumefaciens*, such as the octopine synthetase and nopaline synthetase termination regions. See also Guerineau et al. (1991) *Mol. Gen.*

Genet. 262:141; Proudfoot (1991) Cell 64:671; Sanfacon et al. (1991) Genes Dev. 5:141; Mogen et al. (1990) Plant Cell 2:1261; Munroe et al. (1990) Gene 91:151; Ballas et al. (1989) Nucleic Acids Res. 17:7891; and Joshi et al. (1987) Nucleic Acids Res. 15:9627. Additional exemplary termination sequences are the pea RubP carboxylase small subunit termination sequence and the Cauliflower Mosaic Virus 35S termination sequence. Other suitable termination sequences will be apparent to those skilled in the art.

Alternatively, the polynucleotides of interest can be provided on any other suitable expression cassette known in the art.

The expression cassettes may contain more than one polynucleotide to be transferred and expressed in the transformed plant. Thus, each nucleic acid sequence will be operably linked to 5' and 3' regulatory sequences. Alternatively, multiple expression cassettes may be provided.

The expression cassette may comprise a selectable marker gene for the selection of transformed cells or tissues. Selectable marker genes include genes encoding antibiotic resistance, such as those encoding neomycin phosphotransferase II (NEO) and hygromycin phosphotransferase (HPT), as well as genes conferring resistance to herbicidal compounds. Herbicide resistance genes generally code for a modified target protein insensitive to the herbicide or for an enzyme that degrades or detoxifies the herbicide in the plant before it can act. See DeBlock et al. (1987) EMBO J. 6:2513; DeBlock et al. (1989) Plant Physiol. 91:691; Fromm et al. (1990) BioTechnology 8:833; Gordon-Kamm et al. (1990) Plant Cell 2:603; and Frisch et al. (1995) Plant Mol. Biol. 27:405-9. For example, resistance to glyphosphate or sulfonylurea herbicides has been obtained using genes coding for the mutant target enzymes, 5-enolpyruvylshikimate-3-phosphate synthase (EPSPS) and acetolactate synthase (ALS). Resistance to glufosinate ammonium, boromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides.

For purposes of the present invention, selectable marker genes include, but are not limited to, genes encoding neomycin phosphotransferase II (Fraley et al. (1986) CRC Critical Reviews in Plant Science 4:1); neomycin phosphotransferase III (Frisch et al. (1995) Plant Mol. Biol. 27:405-9); cyanamide hydratase (Maier-Greiner et al. (1991) Proc. Natl. Acad. Sci. USA 88:4250); aspartate kinase; dihydrodipicolinate synthase (Perl et al. (1993) BioTechnology 11:715); bar gene (Toki et al. (1992) Plant Physiol. 100:1503; Meagher et al. (1996) Crop Sci. 36:1367); tryptophan decarboxylase (Goddijn et al. (1993) Plant Mol. Biol. 22:907); neomycin phosphotransferase (NEO; Southern et al. (1982) J. Mol. Appl. Gen. 1:327); hygromycin phosphotransferase (HPT or HYG; Shimizu et al. (1986) Mol. Cell. Biol. 6:1074); dihydrofolate reductase (DHFR; Kwok et al. (1986) Proc. Natl. Acad. Sci. USA 83:4552); phosphinothricin acetyltransferase (DeBlock et al. (1987) EMBO J. 6:2513); 2,2-dichloropropionic acid dehalogenase (Buchanan-Wollatron et al. (1989) J. Cell. Biochem. 13D:330); acetohydroxyacid synthase (U.S. Pat. No. 4,761,373 to Anderson et al.; Haughn et al. (1988) Mol. Gen. Genet. 221:266); 5-enolpyruvyl-shikimate-phosphate synthase (aroA; Comai et al. (1985) Nature 317:741); haloarylnitrilase (WO 87/04181 to Stalker et al.); acetyl-coenzyme A carboxylase (Parker et al. (1990) Plant Physiol. 92:1220); dihydropteroate synthase (sulI; Guerineau et al. (1990) Plant Mol. Biol. 15:127); and 32 kDa photosystem II polypeptide (psbA; Hirschberg et al. (1983) Science 222:1346 (1983).

Also included are genes encoding resistance to: gentamycin (e.g., aacC1, Wohlleben et al. (1989) Mol. Gen. Genet. 217:202-208); chloramphenicol (Herrera-Estrella et al. (1983) EMBO J. 2:987); methotrexate (Herrera-Estrella et al. (1983) Nature 303:209; Meijer et al. (1991) Plant Mol. Biol. 16:807); hygromycin (Waldron et al. (1985) Plant Mol. Biol. 5:103; Zhijian et al. (1995) Plant Science 108:219; Meijer et al. (1991) Plant Mol. Bio. 16:807); streptomycin (Jones et al. (1987) Mol. Gen. Genet. 210:86); spectinomycin (Bretagne-Sagnard et al. (1996) Transgenic Res. 5:131); bleomycin (Hille et al. (1986) Plant Mol. Biol. 7:171); sulfonamide (Guerineau et al. (1990) Plant Mol. Bio. 15:127); bromoxynil (Stalker et al. (1988) Science 242:419); 2,4-D (Streber et al. (1989) BioTechnology 7:811); phosphinothricin (DeBlock et al. (1987) EMBO J. 6:2513); spectinomycin (Bretagne-Sagnard and Chupeau, Transgenic Research 5:131).

The bar gene confers herbicide resistance to glufosinate-type herbicides, such as phosphinothricin (PPT) or bialaphos, and the like. As noted above, other selectable markers that could be used in the vector constructs include, but are not limited to, the pat gene, also for bialaphos and phosphinothricin resistance, the ALS gene for imidazolinone resistance, the HPH or HYG gene for hygromycin resistance, the EPSP synthase gene for glyphosate resistance, the Hm1 gene for resistance to the Hc-toxin, and other selective agents used routinely and known to one of ordinary skill in the art. See Yarranton (1992) Curr. Opin. Biotech. 3:506; Chistopherson et al. (1992) Proc. Natl. Acad. Sci. USA 89:6314; Yao et al. (1992) Cell 71:63; Reznikoff (1992) Mol. Microbiol. 6:2419; Barkley et al. (1980) The Operon 177-220; Hu et al. (1987) Cell 48:555; Brown et al. (1987) Cell 49:603; Figge et al. (1988) Cell 52:713; Deuschle et al. (1989) Proc. Natl. Acad. Sci. USA 86:5400; Fuerst et al. (1989) Proc. Natl. Acad. Sci. USA 86:2549; Deuschle et al. (1990) Science 248:480; Labow et al. (1990) Mol. Cell. Biol. 10:3343; Zambretti et al. (1992) Proc. Natl. Acad. Sci. USA 89:3952; Baim et al. (1991) Proc. Natl. Acad. Sci. USA 88:5072; Wyborski et al. (1991) Nuc. Acids Res. 19:4647; Hillenand-Wissman (1989) Topics in Mol. And Struc. Biol. 10:143; Degenkolb et al. (1991) Antimicrob. Agents Chemother. 35:1591; Kleinschnidt et al. (1988) Biochemistry 27:1094; Gatz et al. (1992) Plant J. 2:397; Gossen et al. (1992) Proc. Natl. Acad. Sci. USA 89:5547; Oliva et al. (1992) Antimicrob. Agents Chemother. 36:913; Hlavka et al. (1985) Handbook of Experimental Pharmacology 78; and Gill et al. (1988) Nature 334:721. Such disclosures are herein incorporated by reference.

The above list of selectable marker genes are not meant to be limiting. Any lethal or non-lethal selectable marker gene can be used in the present invention.

C. Modification of Nucleotide Sequences for Enhanced Expression in a Host Cell

The present invention provides for the modification of the polynucleotide to enhance its recombinant production in a host cell. One such modification is the synthesis of the nucleotide sequence of interest using codons preferred in the host cell. Methods are available in the art for synthesizing nucleotide sequences with host-preferred codons. See, e.g., U.S. Pat. Nos. 5,380,831 and 5,436,391; Perlak et al. (1991) Proc. Natl. Acad. Sci. USA 15:3324; Iannacome et al. (1997) Plant Mol. Biol. 34:485; and Murray et al., (1989) Nucleic Acids. Res. 17:477, herein incorporated by reference. The preferred codons may be determined from the codons of highest frequency in the proteins expressed in the host cell. All or any part of the polynucleotide may be optimized or synthetic. In other words, fully optimized or partially optimized sequences may also be used. For example, 40%, 45%, 50%, 55%, 60%, 65%, 70%, 75%, 80%, 85%, 87%, 90%, 91%, 92%, 93%, 94%, 95%, 96%, 97%, 98%, 99%, or 100% of the codons may be host cell-preferred codons. In one embodiment, between 90 and 96% of the codons are host cell-preferred codons.

Other modifications can also be made to the nucleotide sequence of interest to enhance its expression in a host cell. These modifications include, but are not limited to, elimination of sequences encoding spurious polyadenylation signals, exon-intron splice site signals, transposon-like repeats, and other such well characterized sequences which may be deleterious to gene expression. The G-C content of the sequence may be adjusted to levels average for a given cellular host, as calculated by reference to known genes expressed in the host cell. When possible, the sequence may be modified to avoid predicted hairpin secondary mRNA structures.

Expression of a transgene in a host cell can also be enhanced by the use of 5' leader sequences. Such leader sequences can act to enhance translation. Translation leaders are known in the art and include, but are not limited to, picornavirus leaders, e.g., EMCV leader (Encephalomyocarditis 5' noncoding region; Elroy-Stein et al. (1989) *Proc. Natl. Acad. Sci USA* 86:6126); potyvirus leaders, e.g., TEV leader (Tobacco Etch Virus; Allison et al. (1986) *Virology* 154:9); human immunoglobulin heavy-chain binding protein (BiP; Macajak and Sarnow (1991) *Nature* 353:90); untranslated leader from the coat protein mRNA of alfalfa mosaic virus (AMV RNA 4; Jobling and Gehrke (1987) *Nature* 325:622); tobacco mosaic virus leader (TMV; Gallie (1989) *Molecular Biology of RNA*, 23:56); potato etch virus leader (Tomashevskaya et al. (1993) *J. Gen. Virol.* 74:2717-2724); Fed-1 5' untranslated region (Dickey (1992) *EMBO J.* 11:2311-2317); RbcS 5' untranslated region (Silverthorne et al. (1990) *J. Plant. Mol. Biol.* 15:49-58); and maize chlorotic mottle virus leader (MCMV; Lommel et al. (1991) *Virology* 81:382). See also, Della-Cioppa et al. (1987) *Plant Physiology* 84:965. Leader sequence comprising plant intron sequence, including intron sequence from the maize dehydrogenase 1 gene, the castor bean catalase gene, or the Arabidopsis tryptophan pathway gene PAT1 has also been shown to increase translational efficient in plants (Callis et al. (1987) *Genes Dev.* 1:1183-1200; Mascarenhas et al. (1990) *Plant Mol. Biol.* 15:913-920). Other leader sequences that may be used include the leader from the *Lemna gibba* ribulose-bisphosphate carboxylase small subunit 5B gene (Buzby et al. (1990) *Plant Cell* 2:805-814).

D. Signal Peptides

Secreted proteins including interferon are usually translated from precursor polypeptides that include a "signal peptide" that interacts with a receptor protein on the membrane of the endoplasmic reticulum to direct the translocation of the growing polypeptide chain across the membrane and into the endoplasmic reticulum for secretion from the cell. This signal peptide is often cleaved from the precursor polypeptide to produce a "mature" polypeptide lacking the signal peptide. In an embodiment of the present invention, a biologically active interferon variant is expressed in duckweed from a polynucleotide that is operably linked with a nucleotide sequence encoding a signal peptide that directs secretion of the interferon variant from the host cell. Any signal peptide known in the art can be used according to the present invention. Plant signal peptides that target protein translocation to the endoplasmic reticulum (for secretion into the apoplast or outside of the cell) are known in the art. See, for example, U.S. Pat. No. 6,020,169 to Lee et al. Alternatively, a mammalian signal peptide can be used to target recombinant interferon variants expressed in a host cell for secretion. In one embodiment of the present invention, the mammalian signal peptide that targets polypeptide secretion is the human α-2b-interferon signal peptide (amino acids 1-23 of NCBI Protein Accession No. AAB59402 and SEQ ID NO:12).

In one embodiment, the nucleotide sequence encoding the signal peptide is modified for enhanced expression in the host cell, utilizing any modification or combination of modifications disclosed in section C above for the polynucleotides of interest.

The secreted biologically active polypeptide can be harvested from the host cell or host cell culture medium by any conventional means known in the art and purified by chromatography, electrophoresis, dialysis, solvent-solvent extraction, and the like.

E. Host cells

In some embodiments, the invention encompasses host cells containing the expression cassettes of the invention. These host cells may be used to recombinantly produce the α-interferon variants. The host cell is one that can transcribe the polynucleotide and can be prokaryotic (for example, *E. coli*) or eukaryotic (for example a plant, yeast, insect, or mammalian cell). Suitable host cells are discussed further in Goeddel, *Gene Expression Technology: Methods in Enzymology* 185, Academic Press, San Diego, Calif. (1990). Methods of transforming such host cells with a nucleic acid molecule are well known in the art.

In some embodiments, the host cells are plant cells. Both monocot cells and dicot cells may be used. Suitable methods of introducing polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058).

In particular embodiments, the host cells for recombinant expression of the α-interferon variants are duckweed cells. Stably transformed duckweed cells may also be obtained according any method known in the art. See, for example, U.S. Pat. No. 6,040,498, and PCT publications WO0210414 and WO02097433.

When the host cell is a plant cell, transgenic plants can be regenerated from transformed host cells.

F. Pharmaceutical Compositions

The α-interferon variants of the invention can be incorporated into pharmaceutical compositions. Such compositions typically include one or more α-interferon variant polypeptides and a pharmaceutically acceptable carrier. The phrase "pharmaceutically acceptable carrier" as used herein is a carrier that is conventionally used in the art to facilitate the storage, administration, and/or the healing effect of the therapeutic ingredients. A carrier may also reduce any undesirable side effects of the α-interferon.

A carrier should be stable (i.e., incapable of reacting with other ingredients in the composition), and it should not produce adverse effects in patients at the dosages and concentrations employed for treatment. Suitable carriers include large stable macromolecules such as albumin, gelatin, collagen, polysaccharide, monosaccharides, polyvinyl-pyrrolidone, polylactic acid, polyglycolic acid, polymeric amino acids, fixed oils, ethyl oleate, liposomes, glucose, sucrose, lactose, mannose, dextrose, dextran, cellulose, sorbitol, polyethylene glycol (PEG), and the like. Slow-release carriers, such as hyaluronic acid, may also be suitable.

Other acceptable components in the composition include, but are not limited to, pharmaceutically acceptable agents that modify isotonicity including water, salts, sugars, polyols, amino acids, and buffers. Examples of suitable buffers include phosphate, citrate, succinate, acetate, and other organic acids or their salts and salts that modify the tonicity such as sodium chloride, sodium phosphate, sodium sulfate, potassium chloride, and can also include the buffers listed above.

The pharmaceutical composition may additionally comprise a solubilizing agent or solubility enhancer. Examples of such solubility enhancers are described, for example, in Wang et al. (1980) *J. Parenteral Drug Assoc.* 34:452-462; herein incorporated by reference.

Non-limiting examples of solubilizing agents encompassed by the present invention include surfactants (detergents) that have a suitable hydrophobic-hydrophilic balance to solubilize interferon. Strong natural or synthetic anionic surfactants such as alkali metal salts of fatty acids and alkali metal alkyl sulfates may be used. Examples of other solubilizing agents that can be used in compositions of the invention include but are not limited to sodium dodecyl sulfonate, sodium decyl sulfate, sodium tetradecyl sulfate, sodium tridecyl sulfonate, sodium myristate, sodium caproylate, sodium dodecyl N-sarcosinate, and sodium tetradecyl N-sarcosinate. Classic stabilization of pharmaceuticals by surfactants or emulsifiers is described, for example, in Levine et al. (1991) *J. Parenteral Sci. Technol.* 45(3):160-165. Additional suitable surfactants are discussed in U.S. Pat. No. 5,935,566, herein incorporated by reference.

In addition to those agents disclosed above, other stabilizing agents, such as ethylenediaminetetracetic acid (EDTA) or one of its salts such as disodium EDTA, can be added to further enhance the stability of the pharmaceutical compositions. The EDTA acts as a scavenger of metal ions known to catalyze many oxidation reactions, thus providing an additional stabilizing agent.

Where the composition is used for delivery to a mammal such as a human, the isotonicity of the composition is also a consideration. Thus, in one embodiment, the composition for an injectable solution will provide an isotonicity the same as, or similar to, that of patient serum or body fluids. To achieve isotonicity, a salt, such as sodium chloride, potassium, chloride, or a phosphate buffer, can be added to the solution at an appropriate concentration.

The pH of the composition is also a consideration. The compositions of the invention have a pH ranging from about 4.0 to about 8.5. Suitable pH ranges include, for example, about 4.5 to about 7.8 or about 5.0 to about 7.5 such as about 6.0, about 6.2, about 6.4, about 6.6, about 6.7, about 6.8, about 6.9, about 7.0, about 7.1, about 7.2, about 7.3, about 7.4, about 7.5, or about 7.6.

A thorough discussion of formulation and selection of pharmaceutically acceptable carriers, stabilizers, etc. can be found in *Remington's Pharmaceutical Sciences* (1990) (18th ed., Mack Pub. Co., Eaton, Pa.), herein incorporated by reference.

EXPERIMENTAL

The following examples are offered for purposes of illustration, not by way of limitation.

Expression Vectors

The expression vector pBMSP-1 used in some of the examples is described in U.S. Pat. No. 5,955,646, herein incorporated by reference. The pBMSP-1 transcriptional cassette contains three copies of a transcriptional activating nucleotide sequence derived from the *Agrobacterium tumefaciens* octopine synthase and, an additional transcriptional activating nucleotide sequence derived from the *Agrobacterium tumefaciens* mannopine synthase gene, a promoter region derived from the *Agrobacterium tumefaciens* mannopine synthase gene, a polylinker site for insertion of the nucleotide sequence encoding the polypeptide of interest, and a termination sequence derived from the *Agrobacterium tumefaciens* nopaline synthase gene (see, van Engelen et al. (1995) 4:288-290; Ni et al. (1995) *Plant J.* 7:661-76; and Luehrsen et al. (1991) *Mol. Gen. Genet.* 225:81-93, each of which is herein incorporated by reference). The pBMSP-1 expression vector also contains a nucleotide sequence coding for neomycin phosphotransferase II as a selectable marker. Transcription of the selectable marker sequence is driven by a promoter derived from the *Agrobacterium tumefaciens* nopaline synthase gene.

The expression vector pBMSP-3, also used in some of the following examples, contains the components of the pBMSP-1 expression vector described above and additionally contains a nucleotide sequence corresponding to nucleotides 1222-1775 of the maize alcohol dehydrogenase gene (GenBank Accession Number X04049) inserted between the promoter and the polylinker.

Expression Constructs for the Production of Human α-2b-Interferon in Duckweed

Table 2 shows the expression constructs used for the production of human α-interferon in duckweed.

TABLE 2

| Construct Name | Expression Vector | Signal Peptide | Interferon-encoding Sequence |
| --- | --- | --- | --- |
| IFN01 | pBMSP-1 | None | Non-optimized human α-2b-interferon |
| IFN02 | pBMSP-3 | Non-optimized human α-2b-interferon signal peptide | Non-optimized human α-2b-interferon |
| IFN03 | pBMSP-3 | *Arabidopsis thaliana* endochitinase signal peptide (nucleotides 338-399 of GenBank Accession number AB023460 with an additional "A" added to the 3' end of the sequence) | Non-optimized human α-2b-interferon |

TABLE 2-continued

| Construct Name | Expression Vector | Signal Peptide | Interferon-encoding Sequence |
|---|---|---|---|
| IFN05 | pBMSP-3 | Modified rice α-amylase signal peptide* | Non-optimized human α-2b-interferon |
| IFN07 | pBMSP-3 | Wild type rice α-amylase signal peptide (nucleotides 34-126 of GenBank Accession No. M24286) | Non-optimized human α-2b-interferon |
| IFN08 | pBMSP-3 | Duckweed codon optimized wild type rice α-amylase signal peptide | Non-optimized human α-2b-interferon |
| IFN09 | pBMSP-3 | Duckweed codon optimized wild type rice α-amylase signal peptide | Duckweed codon optimized human α-2b-interferon |
| IFN10 | pBMSP-3 | None | Duckweed codon optimized human α-2b-interferon |
| IFN11 | pBMSP-1 | Duckweed codon optimized wild type rice α-amylase signal peptide | Duckweed codon optimized human α-2b-interferon |
| IFN12 | pBMSP-1 | None | Duckweed codon optimized human α-2b-interferon |
| IFN053 | modified pBMSP-3** | Duckweed codon optimized wild type rice α-amylase signal peptide | Duckweed codon optimized human α-2b-interferon |

*The nucleotide sequence encoding the modified rice α-amylase signal peptide corresponds to nucleotides 34-126 of NCBI Accession No. M24286, except that nucleotides 97-102 have been changed from "CTTGGC" to "ATCGTC."
**For construct IFN053, the 5'-mas leader in pBMPSP3 was replaced with the leader from the ribulose-bis-phosphate carboxylase small subunit 5B gene of *Lemna gibba* (nucleotides 689-751 of NCBI Accession No. S45167, Buzby et al. (1990) Plant Cell 2: 805-814).

Transformation of Duckweed

Duckweed fronds or duckweed nodule cultures (derived from *Lemna minor* strain 8627 in these examples) were transformed with the expression constructs described above using Agrobacteria-mediated transformation methods. *Agrobacterium tumefaciens* strain C58Z707, a disarmed, broad host range C58 strain (Hepburn et al. (1985) *J. Gen. Microbiol.* 131:2961-2969) is used for transformation in these examples. The expression constructs described above were mobilized into *A. tumefaciens* by electroporation, or by a triparental mating procedure using *E. coli* MM294 harboring the mobilizing plasmid pRK2013 (Hoekema et al. (1983) *Nature* 303: 179-180; Ditta et al. (1980) *Proc. Natl. Acad. Sci. USA* 77: 7347-7350). C58Z707 strains comprising the expression constructs described above are streaked on AB minimal medium (Chilton et al., (1974) *Proc. Nat. Acad. Sci. USA* 71: 3672-3676) or in YEB medium (1 g/L yeast extract, 5 g/L beef extract, 5 g/L peptone, 5 g/L sucrose, 0.5 g/L $MgSO_4$) containing streptomycin at 500 mg/L, spectinomycin at 50 mg/L and kanamycin sulfate at 50 mg/L and grown overnight at 28° C.

In these examples, *Lemna minor* strain 8627 was used for transformation although any *Lemna* strain can be used. Fronds were grown on liquid Schenk and Hildebrandt medium (Schenk and Hildebrandt (1972) *Can. J. Bot.* 50:199) containing 1% sucrose and 10 μM indoleacetic acid at 23° C. under a 16-hour light/8-hour dark photoperiod with light intensity of approximately 40 μM/m²·sec. For inoculation, individual fronds were separated from clumps and floated in inoculation media for approximately 2 to 20 minutes. The inoculating medium is Schenk and Hildebrandt medium (pH 5.6) supplemented with 0.6 M mannitol and 100 μM acetosyringone, with the appropriate *Agrobacterium tumefaciens* strain comprising the expression construct present at a concentration of about 1×10⁹ cells/ml. These fronds were then transferred to Schenk and Hildebrandt medium (pH 5.6) containing 1% sucrose, 0.9% agar, and 20 mg/L acetosyringone and are co-cultivated for 3 or 4 days in the dark at 23° C.

Following co-cultivation, the fronds were transferred for recovery to Schenk and Hildebrandt medium or Murashige and Skoog medium (Murashige and Skoog (1962) *Physiol. Plant.* 15:473) supplemented with 200 μg/ml kanamycin sulfate. Fronds wre decontaminated from infecting Agrobacteria by transferring the infected tissue to fresh medium with antibiotic every 2-4 days. The fronds were incubated on this medium for approximately four weeks under conditions of low light (1-5 μM/m²·sec).

Duckweed nodule cultures for transformation were produced as follows. Duckweed fronds are separated, the roots are cut off with a sterile scalpel, and the fronds are placed, ventral side down, on Murashige and Skoog medium (catalog number M-5519; Sigma Chemical Corporation, St. Louis, Mo.) pH 5.6, supplemented with 5 μM 2,4-dichlorophenoxyacetic acid, 0.5 μM 1-Phenyl-3(1,2,3-thiadiazol-5-yl) urea thidiazuron (Sigma P6186), 3% sucrose, 0.4 Difco Bacto-agar (Fisher Scientific), and 0.15% Gelrite (Sigma). Fronds are grown for 5-6 weeks. At this time, the nodules (small, yellowish cell masses) appeared, generally from the central part of the ventral side. This nodule tissue was detached from the mother frond and cultured in Murashige and Skoog medium supplemented with 3% sucrose, 0.4% Difco Bacto-agar, 0.15% Gelrite, 1 μM 2,4-dichlorophenoxyacetic acid, and 2 μM benzyladenine.

Duckweed nodule cultures were transformed as follows. The appropriate *Agrobacterium tumefaciens* strain is grown on potato dextrose agar or YEB agar with 50 mg/L kanamycin and 100 μM acetosyringone, and resuspended in Murashige and Skoog medium supplemented with 0.6 M Mannitol and 100 μM acetosyringone. Nodule culture tissue was inoculated by immersing in the solution of resuspended bacteria for 1-2 minutes, blotted to remove excess fluid, and plated on co-cultivation medium consisting of Murashige and Skoog medium supplemented with auxin and cytokinin optimized to promote nodule growth and 100 μM acetosyringone. See, Yamamoto et al. (2001) *In Vitro Cell Dev. Biol. Plant* 37:349-353.

For selection, nodule culture tissue was transferred to regeneration medium Murashige and Skoog medium with 3% sucrose, 1 μM 2,4-dichlorophenoxyacetate, 2 μM benzyladenine, 0.4% Difco Bacto-Agar, 0.15% Gelrite 500 mg/L cefotaxime, and 200 mg/L kanamycin sulfate and cultured for approximately four weeks under continuous light (20-40 μM/m² sec). The nodule tissue was transferred every 7 days to fresh culture medium. Selection is complete when the nodule tissue shows vigorous growth on the selection agent. In some examples, the transformed duckweed nodule cultures are transferred directly to regeneration medium for selection, instead of undergoing selection in co-cultivation medium.

For regeneration of transformed duckweed, the selected nodule culture was transferred to regeneration medium (0.5× Schenk and Hildebrandt medium supplemented with 1% sucrose and 200 mgs/L kanamycin) to organize and produce plants. The nodule culture is incubated on regeneration medium under full light for approximately 3 weeks, until fronds appear. Fully organized fronds were transferred to liquid Schenk and Hildebrandt medium with 1-3% sucrose and incubated under full light for further clonal proliferation. Detection of Biologically-Active Interferon Produced from Duckweed Fronds or Duckweed Nodule Culture Biologically-active interferon was detected by various assays, including a solid phase sandwich immunoassay as described in Staehlin et al. (1981) *Methods Enzymol.* 79:589-594 and Kelder et al. (1986) *Methods Enzymol.* 119:582-587, herein incorporated by reference, and a cytopathic effect inhibition assay (described in Tovey et al. (1978) *Nature* 276:270-272, herein incorporated by reference. Secreted interferon was collected from the duckweed culture medium, while non-secreted interferon was collected from ground-up or lysed duckweed plants or duckweed nodule tissue.

A solid phase sandwich immunoassay for interferon was performed using a kit from PBL Laboratories (New Brunswick, N.J.) according to the manufacturer's instructions. Briefly, interferon is captured by an antibody bound to the microtiter plate wells. A second antibody is then used to reveal the bound antibody. An anti-secondary antibody conjugated to horseradish peroxidase (HRP) is then used to mark the interferon. Tetramethyl benzidine (TMB) initiates a peroxidase-catalyzed color change so that the interferon level can be observed and compared with a standard. A monoclonal antibody specific for α-2b-interferon (Cat. No. 11105, PBL Laboratories) was used for this assay in the present examples.

A cytopathic effect inhibition assay was performed according to the methods of Tovey et al. (1978) *Nature* 276:270-272. Briefly, serial two-fold dilutions of the preparation to be assayed are diluted in a 96 well microtiter plate (Falcon Inc) in a volume of 100 μl of Eagles minimal essential medium (Life Technologies Inc) supplemented with 2% fetal calf serum (Life Technologies Inc) in parallel with serial two fold dilutions of the US National Institutes of Health human IFN alpha international reference preparation (G-002-901-527). Twenty thousand human amnion cells (line WISH) are then added to each well of the microtiter plate in a volume of 100 μl of medium with 2% fetal calf serum. The cells were incubated over-night in an atmosphere of 5% $CO_2$ in air at 37° C., the medium was removed and replaced with 200 μl of medium with 2% fetal calf serum containing vesicular stomatitis virus at a multiplicity of infection of 0.1. The cells were further incubated over-night in an atmosphere of 5% $CO_2$ in air at 37° C. and the cytopathic effect due to virus replication was then evaluated under a light microscope. Interferon titers were expressed as the reciprocal of the IFN dilution which gave 50% protection against the cytopathic effects of the virus. Interferon titers were expressed in international reference units by reference to the titer of the reference preparation.

The following examples demonstrate the expression of biologically active interferon variants in duckweed.

Example 1

A study was performed to determine culture IFN levels in media and tissue at various time points in a batch culture. A set of 20-30 ml 175 oz.-culture jars were inoculated on Day 0 with 20 fronds of a line previously identified as expressing detectable levels of human α-2b-interferon (IFN). The cultures were grown under autotrophic, buffered conditions with continuous high light provided by plant/aquarium fluorescent grow bulbs. At each time point—days 5, 7, 13, 15, and 18—the fresh weight and media volume were measured for four cultures. From each culture, media and tissue samples were obtained and a plant protease inhibitor cocktail was added. The tissue samples were ground and spun cold. The supernatant was collected. Media and tissue extracts were stored at −70° C. until all samples were collected. IFN levels in media and tissue extracts were determined on the same day using the solid phase sandwich immunoassay described above. Total culture IFN in media and tissue was calculated by multiplying measured IFN concentrations and the volume of media and the fresh weight for the culture, respectively. FIG. 1 shows the relative IFN levels on days 7, 13, 15, and 18 compared to day 5. The last time point represents the average value for three cultures instead of four due to loss of one culture.

Example 2

A study was performed to determine culture IFN levels in media and tissue at various time points in a batch culture. A set of 24-30 ml 175 oz.-culture jars were inoculated on Day 0 with 20 fronds of the same line as in Example 1. The cultures were grown under autotrophic, unbuffered conditions with continuous high light provided by plant/aquarium fluorescent grow bulbs. At each time point—days 7, 10, 12, 14, 17, and 19—the fresh weight and media volume were measured for four cultures. From each culture, media and tissue samples were obtained and a plant protease inhibitor cocktail was added. The tissue samples were ground and spun cold. The supernatant was collected. Media and tissue extracts were stored at −70° C. until all samples were collected. IFN levels in media and tissue extracts were determined on the same day using the solid phase sandwich immunoassay described above. Total culture IFN in media and tissue was calculated by multiplying measured IFN concentrations and the volume of media and the fresh weight for the culture, respectively. FIG. 2 shows the relative IFN levels on days 14, 17, and 19 compared to day 12. Media IFN levels on day 7 and day 10 were below the range of the extended range protocol for the immunoassay.

Example 3

Duckweed lines transformed with the expression constructs listed in Table 2 were produced using the methods described above. These transformed duckweed lines were grown for 14 days under autotrophic conditions. Bovine serum albumin at a concentration of 0.2 mg/ml was included in the growth media. On day 14, media and tissue extracts were prepared as described in Example 1, and the interferon levels in these extracts were determined using the solid phase sandwich immunoassay as described above. Table 3 gives the number of clonal duckweed lines assayed and the mean media interferon concentration for each expression construct.

Table 4 shows the interferon levels within the duckweed tissue for the duckweed lines transformed with the interferon expression constructs that did not contain a signal peptide (IFN01, IFN10, and IFN12). Both the mean interferon level for all clonal lines assayed for the designated construct, and the interferon level for the top-expressing line are shown.

TABLE 3

| Expression Construct | # of Clonal Lines Tested | Mean Interferon Concentration (ng/ml) |
| --- | --- | --- |
| IFN01 | 41 | 0 |
| IFN02 | 75 | 2.3 |
| IFN03 | 41 | 0.18 |
| IFN05 | 44 | 2.5 |
| IFN07 | 41 | 1.5 |
| IFN08 | 41 | 1.4 |
| IFN09 | 41 | 30.3 |
| IFN10 | 41 | 0 |
| IFN11 | 39 | 9.9 |
| IFN12 | 41 | 0 |

TABLE 4

| IFN Construct | Mean Value % of total soluble protein | Top Expresser % of total soluble protein |
| --- | --- | --- |
| IFN01 | 0.00003 | 0.0001 |
| IFN10 | 0.00064 | 0.0074 |
| IFN12 | 0.00014 | 0.001 |

The biological activity of the interferon produced by these transformed duckweed lines was assayed by the cytopathic effect inhibition assay described above. Table 5 gives the results for the top expressing line for each construct. The interferon activity is shown for the media for those constructs containing a signal peptide and the tissue for those constructs lacking a signal peptide.

TABLE 5

| | Top Expresser | |
| --- | --- | --- |
| IFN Construct | Source material | IU/ml (media) IU/mg total protein (tissue) |
| IFN01 | Tissue | 40 |
| IFN02 | Media | 16,000 |
| IFN03 | Media | 320 |
| IFN05 | Media | 6,400 |
| IFN07 | Media | 6,000 |
| IFN08 | Media | 3,200 |
| IFN09 | Media | 200,000 |
| IFN10 | Tissue | 19,300 |
| IFN11 | Media | 30,000 |
| IFN12 | Tissue | 150 |

Example 4

A study was performed to determine the levels of IFN expressed from transgenic duckweed grown at bioproduction scales. Transgenic duckweed plants were generated using IFN expression constructs IFN02, IFN05, IFN09, IFN10, and IFN53 (see Table 2).

A minimum of 40 independent transgenic lines was screened for each of these constructs. The lines producing the highest levels of IFN expression were analyzed further. The concentration of IFN in the media and tissue was determined by ELISA as described elsewhere herein.

Table 6 summarizes the IFN expression on both research and bioproduction scales for the constructs described above. Because *Lemna* is unique in that it grows in a very dilute inorganic media with a low protein content, the expression values in this Table are defined by the pre-purification titer. In the case of IFN53, IFN represents over 30% of the total media proteins.

TABLE 6

Expression of IFN in Lemna

| | Media IFN concentration for Top Expressing Line (mg/L)$^c$ | | | Mean Average Concentration for 2 Week Screening Trials (determined by ELISA)$^b$ | |
| --- | --- | --- | --- | --- | --- |
| Expression construct | Research Scale (2 weeks) | Research Scale (3 weeks) | Bio-production Scale | Media (mg/L)$^c$ | Tissue (mg/kg tissue)$^a$ |
| IFN02 | 2.0 | — | — | 0.12 | 23.3 |
| IFN05 | 1.1 | — | — | 0.13 | 86.7 |
| IFN09 | 24.8 | 60 | 30 | 1.51 | 164 |
| IFN10 | <0.1 | — | — | <0.0001 | 99.3 |
| IFN53 | 100 | 300 | 500 | 15.3$^d$ | — |

$^a$Based on 1 g of tissue yielding 20 mg of protein.
$^b$Based on recovery of 10 ml of media and 1 go of tissue per screening trial.
$^c$Expressed as a pre-purification titer.
$^d$1 week screening trial.

The antiviral activity of the duckweed-produced IFN was determined as follows. HuH7 cells were incubated for 24 hours at 37° C. with 1,000 IU/ml of unpurified IFN from the duckweed media or Intron® A (Schering) as a control. The IFN was then removed and the cells were washed twice. The cells were subsequently infected with an RNA virus selected from Encephalomyocarditis virus (EMCV), vesicular stomatitis virus (VSV), or Sindbis at a multiplicity of infection of 1.0 for 1 hour, at which time the virus innoculum was removed. The cells were then washed three times and allowed to grow for 24 hours at 37° C. The cells were harvested, lysed by six freeze/thaw cycles, and then cell debris was removed by centrifugation. Serial dilutions of the virus were then assayed for their cytopathic effect on monkey CV1 Vero cells. The duckweed-produced IFN exhibited similar antiviral activity to that observed for Intron®A.

The antiproliferative activity of the duckweed-produced IFN was determined as follows. Interferon-sensitive Daudi cells were seeded in microtiter plates at an initial concentration of 50,000 cells/ml. The culture were then either left untreated or were treated with 1000 IU of unpurified duckweed-produced IFN, Intron® A, or an equivalent volume of control media derived from non-transgenic plants grown under the same conditions as for the transgenic plants. After four days, the number of viable and dead cells were determined by the trypan blue-exclusion viability test.

Example 5

The sequence of the biologically active α-2b-interferon produced in duckweed was determined by mass spectrometry. The duckweed-produced interferon consisted of a mixture of five different species, with carboxy-terminus truncations of 4-8 amino acids in comparison with wild type human α-2b interferon. No full-length α-2b interferon was detected. The sequences of the variant interferons produced in duckweed are shown in SEQ ID NOS: 6-10. The predominant species produced was the 158 amino acid polypeptide shown in SEQ ID NO:9. The sequences of the corresponding precursor interferon polypeptides containing the human α-2b-interferon signal peptide are shown in SEQ ID NOS:1-5. Although the present invention is not limited to any particular mechanism, it is believed that the interferon variants were produced in duckweed by the action of an endogenous plant protease. It is the novel finding of the present invention that truncated interferon variants having the amino acid sequences shown in SEQ ID NOS:6-10 are biologically active, as shown in the Examples above.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An isolated polynucleotide encoding a polypeptide consisting of the amino acid sequence set forth in SEQ ID NO:10.

2. An isolated polynucleotide encoding a polypeptide consisting of the amino acid sequence set forth in SEQ ID NO:5.

3. An isolated polynucleotide encoding a polypeptide consisting of a signal peptide operably linked to the amino acid sequence set forth in SEQ ID NO:10.

4. An expression cassette comprising the isolated polynucleotide of claim 1.

5. A host plant cell comprising the expression cassette of claim 4.

6. The host plant cell of claim 5, wherein said plant cell is a duckweed cell.

7. The isolated polynucleotide of claim 3, wherein said signal peptide is a plant signal peptide.

8. An expression cassette comprising the isolated polynucleotide of claim 3.

9. A host plant cell comprising the expression cassette of claim 8.

10. The host plant cell of claim 9, wherein said plant cell is a duckweed cell.

* * * * *

UNITED STATES PATENT AND TRADEMARK OFFICE
CERTIFICATE OF CORRECTION

| | | |
|---|---|---|
| PATENT NO. | : 7,959,910 B2 | Page 1 of 1 |
| APPLICATION NO. | : 10/574046 | |
| DATED | : June 14, 2011 | |
| INVENTOR(S) | : Dickey et al. | |

It is certified that error appears in the above-identified patent and that said Letters Patent is hereby corrected as shown below:

Title Page, insert the following:

Item

--Related U.S. Application Data

(60) Claims priority to Application No. 10/675,011, filed on Sep. 30, 2003.--; and Col. 16, line 49, "unpuri fled" should be --unpurified--.

Signed and Sealed this
Eighteenth Day of October, 2011

David J. Kappos
*Director of the United States Patent and Trademark Office*